United States Patent [19]
Schreiber

[11] Patent Number: 4,873,976
[45] Date of Patent: Oct. 17, 1989

[54] SURGICAL FASTENERS AND METHOD

[76] Inventor: Saul N. Schreiber, 6525 N. Central Ave., Phoenix, Ariz. 85012

[21] Appl. No.: 584,464

[22] Filed: Feb. 28, 1984

[51] Int. Cl.⁴ .............................................. A61B 17/04
[52] U.S. Cl. .................................................. 128/334 R
[58] Field of Search ............ 128/339, 340, 337, 335.5, 128/335, 334 R, 334 C, 330, 336; 223/102

[56] References Cited

U.S. PATENT DOCUMENTS

| | | | |
|---|---|---|---|
| 3,166,072 | 1/1965 | Sullivan | 128/346 |
| 3,946,740 | 3/1976 | Bassett | 128/334 R |
| 3,981,051 | 9/1976 | Brumlik | 24/204 |
| 4,006,747 | 2/1977 | Kronenthal et al. | 128/335 |
| 4,060,089 | 11/1977 | Noiles | 128/325 |
| 4,259,959 | 4/1981 | Walker | 128/337 |
| 4,316,469 | 2/1982 | Kapitanov | |

FOREIGN PATENT DOCUMENTS 2740274  3/1978  Fed. Rep. of Germany ...... 128/335

*Primary Examiner*—Michael H. Thaler
*Attorney, Agent, or Firm*—Harry M. Weiss

[57] ABSTRACT

Surgical fasteners and a method for repairing a tear in body tissue using the fastener are disclosed. The fastener includes a suture and an instrument for inserting the suture. The suture has a base member for seating against the body tissue, a shaft upstanding from the base member for inserting into the tissue and across the tear, and at least one barb for locking the shaft in place, holding the sides of the tear together. The surgical fastener is particularly adapted for repairing the meniscus at the knee joint. The meniscus is prepared by removing the tip or inner edge thereof to provide a flat surface through which to insert the suture and against which to seat the base member. The suture is inserted through the prepared surface internal to the joint and is outwardly directed. The suture passes through the tear area and joins together the two sides of the tear.

31 Claims, 2 Drawing Sheets

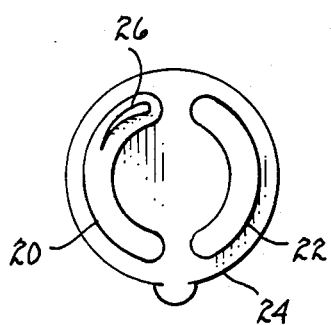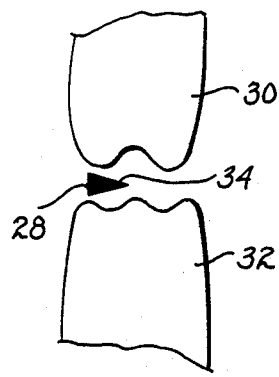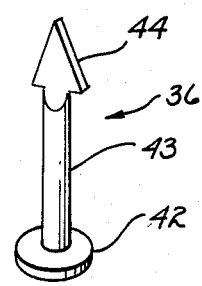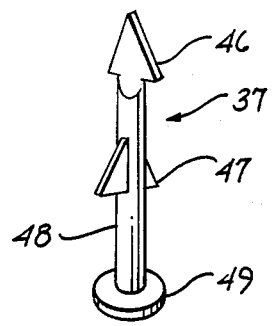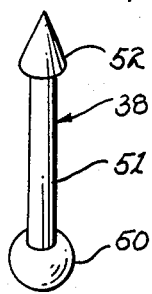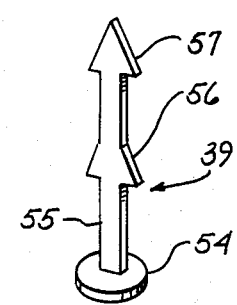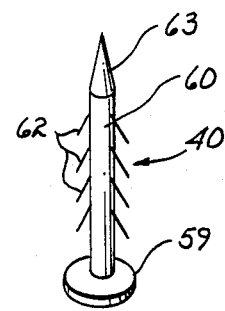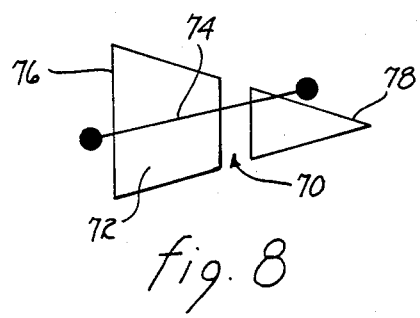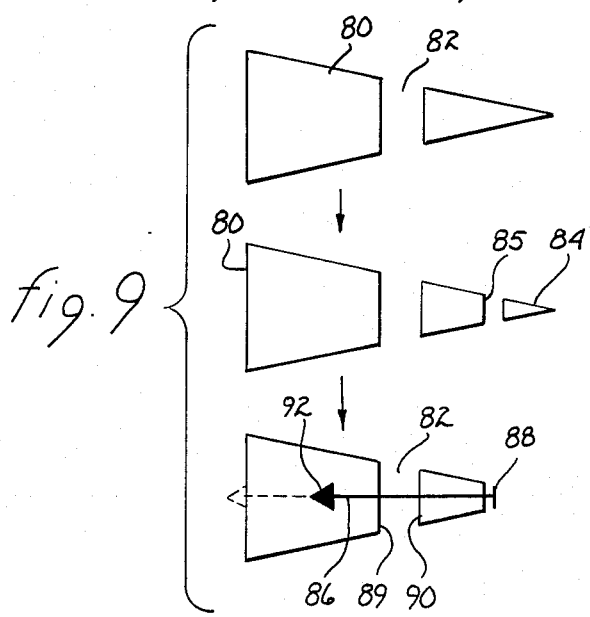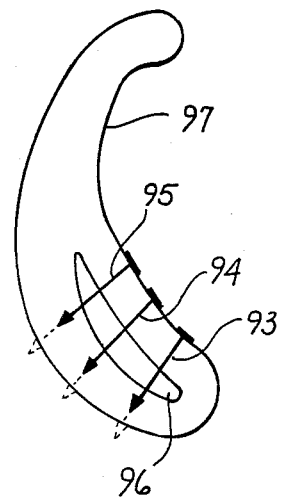

SURGICAL FASTENERS AND METHOD

BACKGROUND OF THE INVENTION

This invention relates generally to surgical fasteners and to methods for repairing body tissue and more specifically to insertable sutures and to methods for repairing meniscus tissue.

There are a number of techniques used for closing incisions, tears, or wounds in body tissue. These techniques include, for example, the use of stitches, staples, clamps, tape, and the like. The technique used in a particluar application depends on the size, nature and location of the opening as well as factors such as necessary haste of repair, strength required, and the like. Despite the wide range of available techniques, however, a need still existed for a surgical fastener and for a method which would provide improved surgical joining of body tissues in certain applications such as in arthroscopic surgery.

There was especially a need for developing a suturing technique that would avoid the undesirable prior technique of, for example, in the case of repairing a meniscus tear in the knee, either (a) making an arthrotomy incision in the knee in order to place a suture into the inner portion of the torn meniscus through to the outer portion, or (b) taking a pair of long needles (which contain a suture between one of the adjacent ends of each needle) and place the two needles through the torn meniscus from the front of the knee joint exiting percutaneously the posterior area of the joint, thereby risking a serious accident or injury to either the neuro-vascular structures or peroneal nerves.

It is therefore an object of this invention to provide an improved surgical fastener.

It is another object of this invention to provide an improved method for repairing openings in body tissue.

It is yet another object of this invention to provide an improved suture and instrument for inserting the suture.

It is still another object of this invention to provide an improved surgical fastener and method for repairing a meniscus tear.

BRIEF SUMMARY OF THE INVENTION

The foregoing and other objects and advantages of the invention are met by the barbed surgical suture and its use as herein described. A suture is provided having a base member, a shaft portion upstanding from the base member, and barbs on the shaft to lock the shaft, once positioned, into tissue being repaired. For the repair of a torn meniscus, for example, the meniscus is prepared for repair by removing the tip of the meniscus to provide a flat surface through which the suture can be inserted and against which the base member can be seated. The suture is inserted through the prepared surface of the meniscus and through the tear to join the opposing edges of the tear.

BRIEF DESCRIPTION OF THE DRAWINGS

FIG. 1 illustrates, in a horizontal section, the position of meniscus on top of a tibial surface, including a representative tear in the medial meniscus;

FIG. 2 illustrates, in a vertical section, the position of a normal meniscus in a knee joint;

FIGS. 3-7 illustrate sutures in accordance with the invention;

FIG. 8 illustrates one difficulty of insertion of a suture into a meniscus;

FIG. 9 illustrates preparation and repair of a torn meniscus in accordance with the invention;

FIG. 10 illustrates repair of a torn meniscus with a plurality of sutures in accordance with the invention;

DETAILED DESCRIPTION OF THE INVENTION

Figure 11:
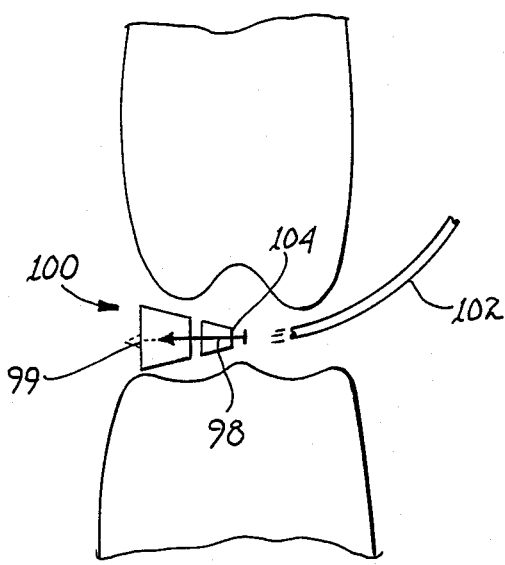
FIG. 11 ilustrates the process of tissue repair.

The invention relates to improved surgical fasteners and, more particularly, to improved insertable sutures and to methods for repairing body tissue using these fasteners. The invention is described, for purposes of illustration only, with reference to the repair of a torn meniscus in a knee joint. The invention is not to be interpreted as being limited to such application.

FIG. 1 illustrates, in horizontal section, the positioning of medial 20 and lateral 22 meniscus on the top of a tibial surface 24. A typical tear in the medial meniscus is indicated at 26. Repair of this tear requires surgical closing to cause the opposing sides of the tear to heal together.

FIG. 2 illustrates, in vertical cross section, the position of a normal meniscus 28 between the femur or thigh bone 30 and tibia or leg bone 32. In cross section the meniscus has a generally triangular shape, with a pointed tip 34.

FIGS. 3-7 illustrate insertable sutures 36, 37, 38, 39, 40 in accordance with various embodiments of the invention. Suture 36 includes a base member 42, a shaft 43 upstanding from the base member, and a flat, triangular shaped barb 44. Base member 42 is adapted for seating securely against the tissue to be repaired. Shaft 43, here illustrated as cylindrical, has sufficient rigidity to be inserted into the body tissue, across the tear or wound. Barb 44, having a width greater than the diameter of shaft 43, locks the shaft into position, once it is inserted into the body tissue.

Sutures in accordance with the invention may have a plurality of barbs to insure the locking in place of the shaft. Suture 37 in FIG. 4 illustrates two barbs 46, 47 which protrude from shaft 48 which, in turn, is upstanding from base member 49. Barbs 46 and 47 are positioned along shaft 48 in planes rotated by about 90 from each other. Base member 49 is a flat cylindrical disc.

FIG. 5 illustrates a further embodiment of the invention. Suture 38 includes a spherical base member 50 from which cylindrical shaft 51 extends. A barb 52 at the end of shaft 51 is conical in shape, having a diameter greater than the diameter of shaft 51.

FIG. 6 illustrates another embodiment of suture in accordance with the invention. Suture 39 includes a base member 54 from which shaft 55 is upstanding. Shaft 55 has a flat, rectangular cross section. Barbs 56 and 57 positioned along shaft 55 have a flat, triangular shape and are coplanar.

FIG. 7 illustrates yet another embodiment of the invention. Suture 40 includes a base member 59 and shaft 60. A plurality of barbs 62 in the form of scales are afixed to shaft 60 and form acute angles with the shaft. A pointed end 63 on shaft 60 facilitates insertion of the suture into the tissue to be repaired.

Sutures, in accordance with the invention, such as those illustrated in FIGS. 3-7, are formed of a material having sufficient rigidity to allow the sutures to be pushed through the tissue to be repaired. The sutures can be formed of metal, plastic, or the like, or, as required, of a material such as "surgical gut" which is slowly but readily absorbable by the body. The sutures are preferably formed in a variety of sizes having shaft lengths of about 4-16 mm, preferably in incremental lengths of about 2 mm. The base members are, likewise, formed in a variety of diameters of about 1-6 mm, preferably in 1 mm increments.

FIG. 8 illustrates one problem encountered in repairing a tear 70 in a meniscus 72. A suture 74, inserted into the meniscus and across the tear, is improperly positioned. The improper positioning is likely to occur whether the suture is inserted through face 76 or whether an attempt is made to insert the suture through pointed tip 78. The difficulty arises from lack of directional control which results either when inserting the suture through the bulk of meniscus 72 from face 76 or from attempting to insert the suture through the pointed tip 78.

FIGS. 9-11 illustrate a method for repairing damaged tissue, specifically a torn meniscus, by using sutures, both method and sutures in accordance with the insertion. FIG. 9 illustrates steps in repairing a meniscus 80 having a tear 82 therein. First the meniscus is prepared for the repair by removing the tip 84. Removing the tip of the meniscus provides a surface 85 through which the suture 86 can be inserted and against which the base 88 of the suture can be seated. The suture is inserted through surface 85 and into meniscus 80, with shaft 91 across tear 82 to join the opposing sides 89, 90 of the tear. Once the suture is properly positioned, barb 92 locks the shaft in position with the opposing sides 89, 90 drawn together. The barb 92 can be either imbedded within the meniscus 80 or, as shown in dotted form, perferably located on an external portion of the meniscus 80.

FIG. 10 illustrates the use of three sutures 93, 94, 95 positioned across tear 96 in meniscus 97. FIG. 11 illustrates a preferred method for inserting a suture 98 into a torn meniscus 99 in knee joint 100. The repair is done arthoscopically, using a light or fiber optic element 102 for observing the repair. The suture is inserted from the central portion of the joint, pointing generally outwardly, using an applicator (not shown) which is inserted generally along side the light or fiber optic element 102. The applicator is described more fully below. The suture is inserted through surface 104 prepared by removing the tip of meniscus 99.

Figure 12:
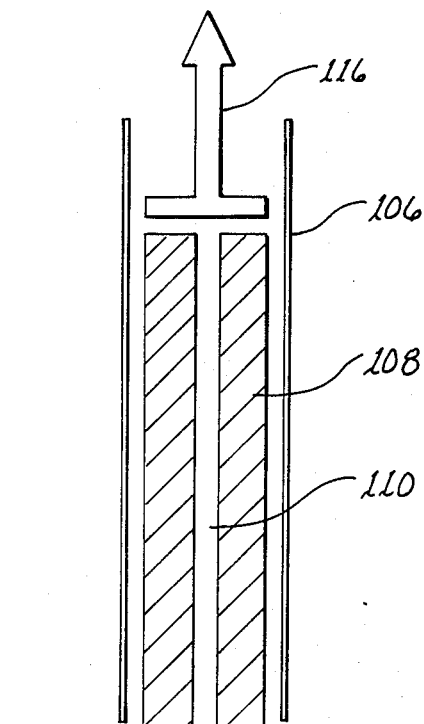
FIGS. 12 and 13 illustrate suture positioning and insertion apparatus.
Figure 13:
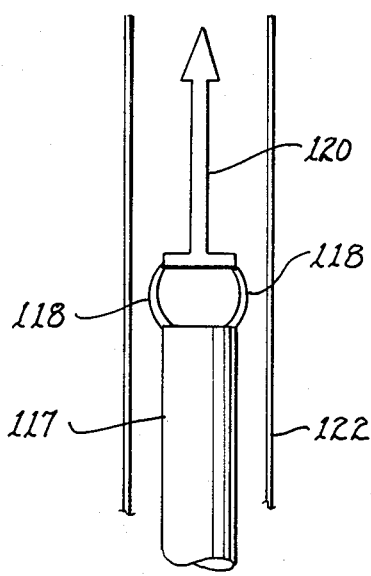

FIGS. 12 and 13 illustrate embodiments of applicators for inserting sutures for the repair of body tissue. FIG. 12 illustrates, in cross section, a preferred embodiment of an applicator including a hollow outer sleeve or cylinder 106 which is inserted, for example, into the central portion of the joint. A pusher 108 of rigid material is sized to fit through the center of hollow cylinder 106. The pusher, in turn, has a central axial hole 110 through the length thereof. The axial hole is provided with a fitting 112 for coupling to a vacuum source (not shown) for providing a reduced pressure within hole 110. The pusher rod and axial hole are also provided with a "thumb hole" 114 which can be covered or opened with the thumb to maintain or release the reduced pressure in the axial hole. Cylinders 106 are provided in a variety of diameters to accomodate sutures 116 of different base diameter. Cylinders 106 and pushers 108 are provided in both straight and curved embodiments for ease of use in various body locations.

As illustrated in FIG. 13, the pusher 117 can, alternatively, be provided with spring grasping means 118 for engaging suture 120 prior to insertion of the suture into the substance of tissue. The springs hold the suture until the pusher and cylinder 122 are withdrawn.

The end of the applicator cylinder or the end of a pushertype rod can be provided with a blade end (not shown) for creating or initiating a channel in the tissue for the suture to pass through. The applicator cylinder is inserted and positioned within the joint cavity, using a light or fiber optic element or other means for insuring the correct positioning. After preparing the tissue for repair, such as by removing the tip of the meniscus, sutures are inserted into the prepared surface using the insertion apparatus described above. The sutures are inserted into the tissue, seating the base of the suture against the tissue and closing the wound.

Thus it is apparent that there has been provided, in accordance with the invention, both suture and method which fully meet the objects and advantages set forth above. Although the invention has been described and illustrated by reference to specific embodiments thereof, it is not intended that the invention be limited to those illustrative embodiments. It will be apparent to those skilled in the art, after review of the foregoing detailed description, that variations and modifications differing from the illustrative embodiment but falling within the spirit of the invention are possible. Accordingly, it is intended that all such variations and modifications be included within the appended claims.

I claim:

1. A single unit suture for body tissue repair comprising:
   a solid base member for seating against an exterior surface of said tissue;
   a single rigid shaft portion upstanding from and integrally connected to said base member adapted for insertion into said tissue; and
   barb means integrally connected to said shaft portion to aid in insertion of said shaft portion into said tissue and to lock said shaft portion into said tissue.

2. The suture of claim 1 wherein said base member has a substantially flat surface.

3. The suture of claim 2 wherein said base member is of substantially circular cross section.

4. The suture of claim 3 wherein said base member has a diameter in the range of about 1-6 mm.

5. The suture of claim 1 wherein said base member is substantially spherical.

6. The suture of claim 1 wherein said shaft portion is substantially cylindrical.

7. The suture of claim 6 wherein said shaft portion has a length in the range of about 4 to about 16 mm.

8. The suture of claim 1 wherein said shaft portion is a substantially flat rectangular shaped portion.

9. The suture of claim 1 wherein said barb means comprises a flat, triangular point at an end of said shaft portion opposite said base member and having a width greater than said shaft portion.

10. The suture of claim 9 further comprising a second triangular barb positioned on said shaft portion between said flat triangular point and said base member.

11. The suture of claim 10 wherein said second barb and said flat triangular point are in substantially the same plane.

12. The suture of claim 10 wherein said second barb and said flat triangular point are in planes about 90 degrees apart.

13. The suture of claim 1 wherein said barb means is located on an external portion of said body tissue.

14. The suture of claim 1 wherein said barb means comprise a plurality of scales positioned at an acute angle with said shaft portion.

15. The suture of claim 1 wherein said base member, shaft portion and barb means comprise a material absorbable by said tissue.

16. A single unit suture for body tissue repair comprising:
  a solid base member having a substantially flat portion for seating against an exterior surface of said tissue;
  a single, rigid cylindrical shaft portion upstanding from and integrally connected to said base member and having a pointed end for insertion into said tissue; and
  barb means positioned along said shaft portion.

17. The suture of claim 16 wherein said barb means comprise conical projections extending from said shaft portion.

18. The suture of claim 16 wherein said barb means comprise triangular projections extending from said shaft portion.

19. A method for repairing a tear in a meniscus which comprises the steps of:
  providing a single unit suture having a solid base member, a single, rigid shaft portion upstanding from and integrally connected to said base member, and barb means located on and integrally connected to said shaft portion;
  preparing the medial surface of said meniscus for insertion of said suture; and
  inserting said suture into said meniscus, through said prepared surface and through said tear to join together opposing edges of said tear for repairing said tear and leaving said base member external to said meniscus.

20. The method of claim 19 wherein said step of preparing the medial surface comprises the step of removing the tip of said meniscus to provide a flat surface portion for engagement contact with said base member of said suture.

21. The method of claim 19 wherein said step of inserting comprises the steps of:
  providing a hollow cylinder for insertion into a joint cavity;
  inserting said suture in said hollow cylinder;
  positioning an end of said hollow cylinder in said joint cavity; and
  propelling said suture through said hollow cylinder and into said meniscus with said hollow cylinder remaining external to said meniscus.

22. The method of claim 21 wherein said step of inserting further comprises providing means for securing said suture within said hollow cylinder and for controllably releasing said suture.

23. The method of claim 19 wherein said step of inserting said suture into said meniscus further comprising the step of inserting said barb means through said meniscus to an external portion thereof.

24. A single unit surgical fastener for repairing a tear in meniscus and like firm body tissue which comprises:
  a single unit suture including a solid base member for seating against said tissue;
  a single, rigid shaft member integrally connected to said base member for insertion into said tissue and across said tear;
  barb means located n said shaft member for locking said shaft member in said tissue and for providing compression between said barb means and said base member;
  a hollow tube for positioning said suture; and
  means for controllably moving said suture through said hollow tube and into said tissue with said hollow tube remaining external to said body tissue.

25. The surgical fastener of claim 24 wherein said suture is comprised of a material absorbable by said body tissue.

26. The surgical fastener of claim 24 wherein said hollow tube is cylindrical having an inner diameter to accommodate said base member.

27. The surgical fastener of claim 26 wherein said means for controllably moving comprises propelling means capable of moving said suture through said hollow tube and means for controllably holding said suture.

28. The surgical fastener of claim 27 wherein said propelling means comprises a rigid pusher rod.

29. The surgical fastener of claim 27 wherein said means for controllably holding comprises vacuum means for holding said base member of said suture against the end of said propelling means.

30. The surgical fastener of claim 29 wherein said vacuum means comprises a vacuum opening through said propelling means;
  means to couple said vacuum opening to a vacuum source; and
  means to maintain or release said vacuum.

31. The surgical fastener of claim 27 wherein said means for controllably holding comprises spring means mounted on the end of said propelling means.

* * * * *